United States Patent [19]

Schubert et al.

[11] Patent Number: 5,151,401
[45] Date of Patent: Sep. 29, 1992

[54] PREPARATION OF DEHYDROGENATING CATALYST

[75] Inventors: Paul F. Schubert, Sunnyvale, Calif.; Donald H. Kubicek, Bartlesville; Dennis R. Kidd, Dewey, both of Okla.

[73] Assignee: Phillips Petroleum Company, Bartlesville, Okla.

[21] Appl. No.: 818,417

[22] Filed: Jan. 6, 1992

Related U.S. Application Data

[63] Continuation of Ser. No. 615,518, Nov. 19, 1990, abandoned.

[51] Int. Cl.$^5$ .................. B01J 37/06; B01J 23/58; B01J 23/60
[52] U.S. Cl. .................................. 502/329; 585/660
[58] Field of Search ............... 502/339, 329, 334, 328, 502/313, 230; 585/230

[56] References Cited

U.S. PATENT DOCUMENTS

| | | | |
|---|---|---|---|
| 2,847,387 | 8/1958 | Smith | 502/334 |
| 3,189,559 | 6/1965 | Doelp et al. | 502/230 |
| 3,649,566 | 3/1972 | Hages et al. | 252/470 |
| 3,852,217 | 12/1974 | Engelhard et al. | 502/230 X |
| 4,048,096 | 9/1977 | Bissot | 252/430 |
| 4,088,736 | 5/1978 | Courty et al. | 423/230 |
| 4,152,365 | 5/1979 | Drehman | 585/660 X |
| 4,370,310 | 1/1983 | Walker | 423/600 |
| 4,431,750 | 2/1984 | McGinnis et al. | 502/329 |
| 4,612,293 | 9/1986 | Johnson | 502/28 |
| 4,902,849 | 2/1990 | McKay et al. | 585/660 |

*Primary Examiner*—W. J. Shine
*Assistant Examiner*—Douglas J. McGinty
*Attorney, Agent, or Firm*—George E. Bogatie

[57] ABSTRACT

Impregnated chloride ions are removed from a chloride containing, platinum on zinc aluminate catalyst support in a specific sequence of operations. In the dechlorination steps, the impregnated platinum is first anchored to the zinc aluminate support in a calcining step, and then the calcined catalyst support is washed with a wash medium to remove the corrosive chloride without removing the platinum catalyst.

12 Claims, 4 Drawing Sheets

PREPARATION OF DEHYDROGENATING CATALYST

This is a continuation of application Ser. No. 07/615,518 filed Nov. 19, 1990, now abandoned.

This invention relates to dehydrogenation catalysts. In one aspect this invention relates to removing chloride from porous catalyst supports which have been impregnated with a solution of a platinum chloride compound. In another aspect, this invention relates to hydrocarbon conversion processes using the platinum catalyst prepared by the novel method.

Platinum catalysts supported on a variety of porous supports have been used in many processes, such as hydrogenation, dehydrogenation, cyclization and various other hydrocarbon conversion processes.

In general, the supported platinum catalyst have been prepared by a variety of processes, such as coprecipitation with the support such as alumina, followed by washing, drying and calcining. Alternatively, the porous support is first formed in any of a variety of discrete forms or pellets, and the porous support is then impregnated with an aqueous solution of a platinum metal compound, such as chloroplatinic acid, and the resulting composite is dried and calcined. Other methods than aqueous impregnation have also been employed, such as the use of a nonaqueous impregnation media with various other compounds.

The prior art methods have provided highly effective catalysts. However, the catalyst preparation processes for the highly effective catalysts usually require process steps which are inherently time consuming and costly. In this regard, a particularly costly process step is the dechlorination of platinum catalyst prepared by impregnating a porous catalyst support with platinum contained in an aqueous solution of chloroplatinic acid. In this process the chloride content of the finished catalyst is in the range of 0.6–0.9 wt % of the support compared to 0.6 wt % of the support of platinum. Dechlorination of the platinum catalyst must therefore be carried out to prevent severe corrosion of downstream equipment.

In the past dechlorination of a supported platinum catalyst containing excessive amounts of chloride was carried out in a costly, high temperature steaming step which required an extended period of time. For example, an effective catalyst dechlorination step required 33 hours of steaming at 1000° F. to achieve less than 0.05 wt % chloride. Thus, it is highly desirable to find a supported platinum catalyst preparation process which lessens the costly, time consuming dechlorination step. We have discovered such a process in which impregnated chloride can be rapidly removed from the catalyst support while retaining essentially all of the impregnated platinum, thus substantially reducing the time and cost of catalyst preparation.

Accordingly, it is an object of this invention to provide an improved method for the manufacture of supported platinum catalyst.

Another object of this invention is to provide a catalyst with proper amounts of tin and platinum promoters while having a low chloride content.

Another object of this invention is to reduce the operating cost of preparing supported platinum catalyst by simplifying the dechlorination of a catalyst which is prepared by impregnating a catalyst support with a chloride containing solution.

Another object of this invention is to provide extruded catalyst supports of sufficient strength, but which are simpler and less expensive to manufacture than tableted catalyst supports.

Still another object of this invention is to prevent corrosion in a reactor containing the catalyst.

SUMMARY OF THE INVENTION

In accordance with this invention, we have discovered an improved process for producing a supported, platinum containing, dehydrogenation catalyst which can be easily dechlorinated after platinum and chloride have been added to the support from a solution containing a platinum chloride compound. The dechlorination is achieved by first drying the platinum chloride impregnated support, followed by calcining at a temperature sufficient to anchor the platinum to the support, and finally subjecting the impregnated, dried and calcined catalyst support to a washing step under conditions sufficient to substantially remove all chloride ions from the support while substantially retaining all of the platinum catalyst deposited on the support, and thereby producing the desired dehydrogenation catalyst.

Further aspects and additional advantages of the present invention will be apparent from the following detailed description of the preferred embodiments of the invention and examples, as illustrated by the drawings in which:

DETAILED DESCRIPTION OF THE PREFERRED EMBODIMENTS

Figure 1:
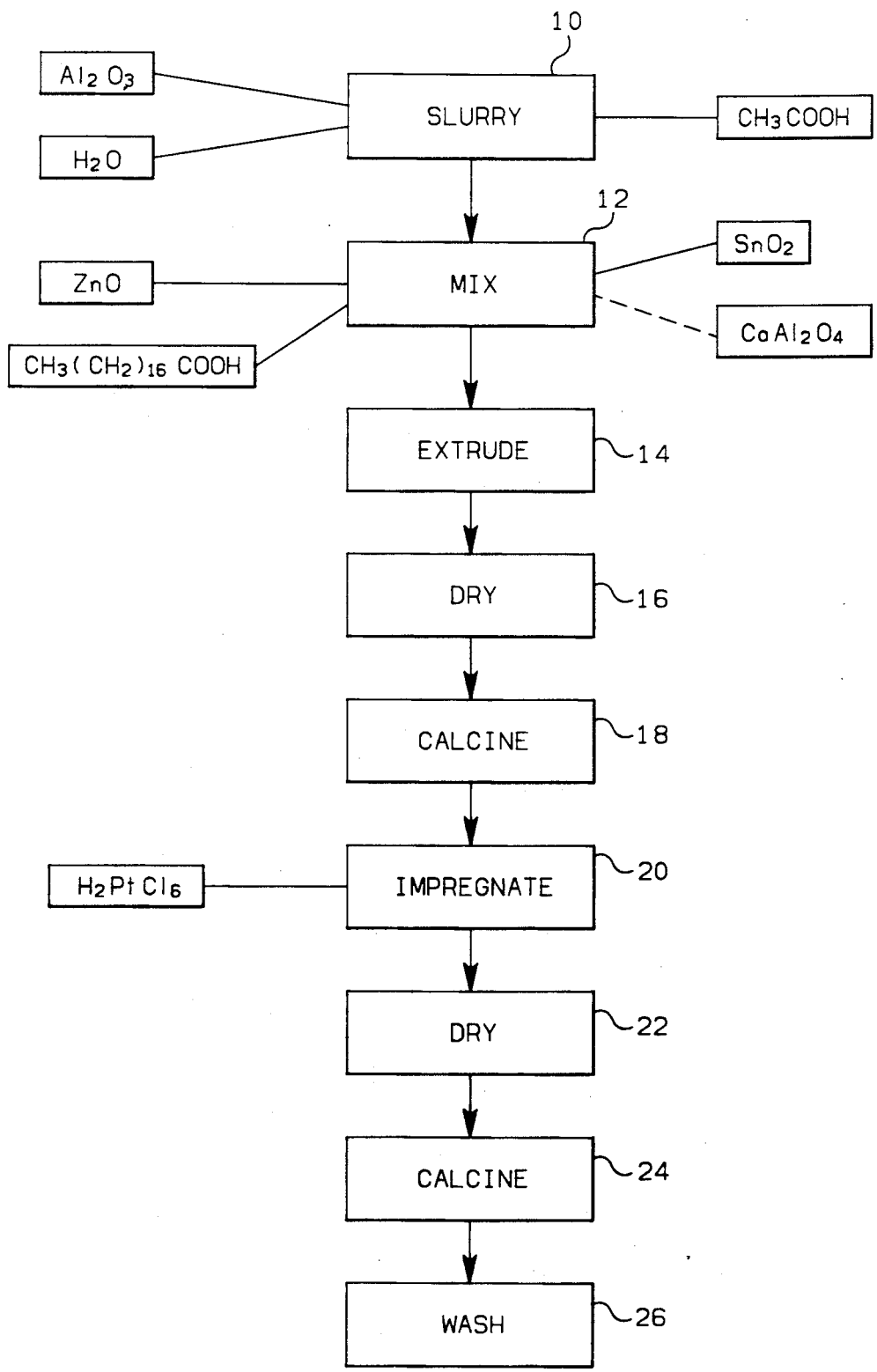
FIG. 1 is a simplified process flow scheme illustrating catalyst preparation according to this invention.

In a preferred embodiment, shown in drawing FIG. 1, a novel method for preparing supported platinum catalyst containing low levels of chloride is illustrated.

The catalyst composition, and the starting compounds used in the preparation of the catalyst composition, employed in this invention, are well known by those familiar in the art and are disclosed in numerous patents such as U.S. Pat. No. 3,880,776 to Box, et al, and U.S. Pat. No. 3,668,151 to Walker which patents are incorporated herein by reference.

The preferred catalysts of this invention are prepared by impregnating a porous support with an aqueous solution of a platinum metal compound. The platinum metal content of the preferred catalyst can be in the range of about 0.01–5 weight percent of the support, and in preferred embodiments is in the range of 0.3–0.6 wt % of the support. Examples of simple platinum compounds that can be used for impregnation are: platinic chloride, chloroplatinic acid, ammonium chloroplatinate, and the like. Chloroplatinic acid, which is very effective, is preferred. When added to the support by impregnation from solution, chloroplatinic acid can be added from an aqueous or alcoholic solution. Examples of materials used for the porous support include alumina, titania, zirconia, magnesia, thoria, chromea, zinc titanate and $SnO/ZnAl_2O_4$.

The catalyst support composition and the starting materials for the catalyst supports are also well known by those skilled in the art and are disclosed in numerous patents such as the aforementioned patents which were incorporated herein by reference. Presently preferred is an extruded support comprising zinc aluminate and tin, in which tin can exist as an oxide in the range of about 0.01-5 weight percent of the support. The support may be prepared from mixtures of finely divided alumina, zinc oxide, and stannic oxide, and with the resulting composition extruded or tableted and then calcined at suitable temperatures. Additional constituents may be added to the support, if desired. Such additional constituents may include various lubricants, cements or other pelletizing additives. For example, calcium aluminate (for a cement) can exist in a range of about 0-50 weight percent, and also stearic acid (octadecanoic acid), graphite or polyethylene fluff can be included for a lubricant in the range of about 1-10 wt. %.

It is the particular sequence of operations performed after the calcined extrudate has been impregnated with platinum and chloride, from a solution containing a platinum chloride compound, that provide the novel features of this invention.

Referring now to FIG. 1, there is illustrated the process flow for catalyst preparation according to this invention. The process begins with operations of a slurry preparation step 10, and a dry mixing step 12, which are employed to obtain a composite composition suitable for extruding.

In the slurry preparation step 10, an alumina slurry is obtained by mixing an alumina, glacial acetic acid and deionized water. In the mixing step 12, particulate zinc oxide, stannic oxide, stearic acid and optionally calcium aluminate are initially dry mixed in suitable proportions as in known in the art, then the slurry prepared in step 10 is slowly added to the dry mixture resulting in a composite composition which is suitable for extruding as illustrated in step 14 of FIG. 1. In some cases step 10 and step 12 can be combined.

The extrudate obtained in step 14 is dried in a first drying step 16, at a temperature of about 228° F. to about 342° F. and the dried extrudate is passed to a first calcining step 18 at a temperature of 1550° F. for a period of 5 hours. The dried and calcined catalyst support is then impregnated with platinum and chloride in any manner known in the art in step 20.

The presently preferred impregnation species for convenience and availability is $H_2PtCl_6$. Impregnation is conducted by treating the selected support with the aqueous solution of chloroplatinic acid at a temperature in the range of about the freezing point to the boiling point of the solution, usually a temperature between about 50°-122° F. is suitable and convenient. Impregnation can be effected at any suitable pressure, generally atmospheric pressure is satisfactory. Time of impregnation can range such as 1 to 1000 seconds, or longer. Usually about 5 to 100 seconds is suitable and convenient.

In accordance with the invention, the impregnated catalyst support, containing chloride, is passed in sequence to the second drying step 22; a second calcining step 24 at a temperature between about 960°-1440° F., and preferably between 1080° and 1190° F., which anchors the platinum to the support; and finally to a washing step 26 to remove the corrosive chloride without removing the platinum catalyst.

Figure 2:
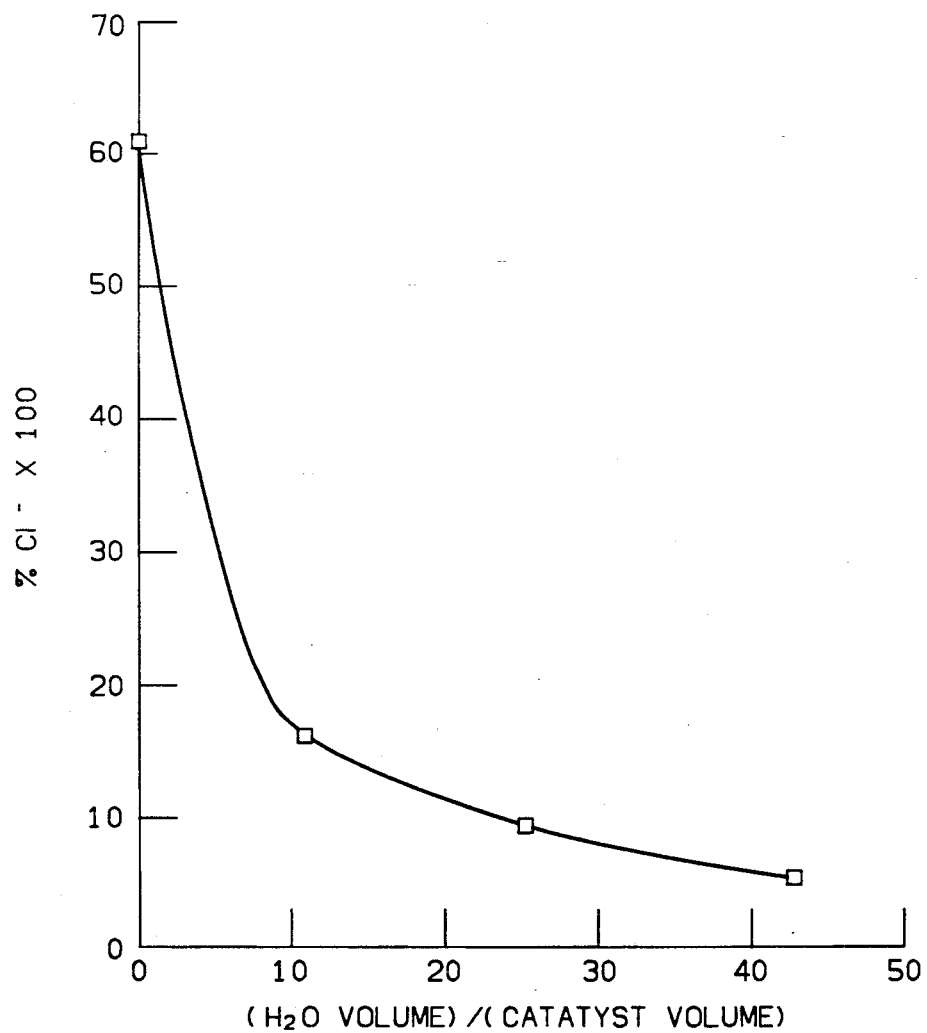
FIG. 2 is a graph illustrating hot water washing of catalyst impregnated with a platinum compound which contains chloride.

Referring now to FIG. 2, there is illustrated a plot of chloride content vs (water volume)/(catalyst volume) for washing the chloride containing catalyst with sufficient wash medium under conditions suitable to remove substantially all chloride ions from the catalyst. Suitable wash media includes water as well as organic solvents in which the chloride ions to be removed from the catalyst are soluble and/or form a complex with the chloride ions such as for example alcohols, esters, ethers, acids and the like, as well as mixtures of any two or more of these media. Water, which is effective, is the preferred media.

The volume of wash media employed is not critical and can readily be determined by those skilled in the art. Generally, at least enough wash media should be employed to thoroughly contact the catalyst being treated. Preferably, sufficient quantity of wash media is employed to also provide a displacement wash, thus aiding in the removal of the chloride ions. In theory there is no upper limit as to the amount of wash media which can be employed. With reference to FIG. 2, however, preferably less than about 40 volumes of water/catalyst volume would be employed to minimize disposal and or recycle considerations. Preferably about 10 to about 30 volumes of wash media per volume of catalyst to be washed will be employed.

The conditions employed for the washing step are not critical and can be readily selected by those of skill in the art. While elevated as well as reduced temperatures can be employed, ambient conditions are preferred since good results are obtained at ambient conditions and minimum energy requirements are placed on the regeneration process when carried out under such conditions.

The supported platinum catalysts prepared according to this invention are suitable for use in a wide variety of chemical and petroleum processes including hydrogenation, hydrocracking, oxidation, cyclization, dehydrogenation, isomerization and the like. These supported catalyst prepared in accordance with the present invention are particularly suitable for the dehydrogenation of alkanes containing from 2 to 12 carbon atoms per molecule. In one embodiment of this invention propane is dehydrogenated to propylene without producing large quantities of undesirable side products.

The following examples illustrate critical catalyst preparation steps and dechlorination steps according to this invention. These examples further illustrate propane dehydrogenation using the catalyst prepared according to this invention, and are intended to further assist one skilled in the art to an understanding of this invention. The examples given, reactants, and conditions are intended to be further exemplary, and not limitative of the reasonable scope of this invention.

EXAMPLE I

Extruded Support

A zinc aluminate support containing stannic oxide and calcium aluminate was prepared by initially dry blending a mixture consisting of 15.6 g of finely divided reagent grade stannic oxide, 472.8 g of finely divided reagent grade zinc oxide, 128.4 g of Secar 71 ® (calcium aluminate cement) and 24 g of stearic acid (lubricant) for 10 minutes in a Lancaster Type PC mixmuller. A slurry obtained by mixing 604.5 g of flame-hydrolyzed alumina with 604 mL of a mixture comprising 102 mL of glacial acetic acid and 1 liter of deionized water was added to the stirred mixture of powders over a 15 minute period. The resulting paste was mixed an additional hour, then immediately extruded through a 1/8 inch die by means of a Baker-Perkins twin-screw extruder operating at 300 rpm. The extrudate having lengths ranging from about 1/4 inch to about 7/8 inch was collected and dried for 20 hours at 575° F. in a forced draft oven. The dried support was subsequently calcined in a muffle furnace for 5 hours at 1550° F. The calculated composition of the calcined support was 88.2 wt % zinc aluminate, 10.5 wt % calcium aluminate and 1.3 wt % stannic oxide. The average crush strength of the calcined extrudate was measured and found to be 12 lbs. Based on mercury porosimetry results the pore volume was found to be 0.37 mL/g, the average pore radius was 290 Angstroms and the pore area was 25.3 m$^2$/g.

EXAMPLE II

Tabletted Support

A double cone blender was employed to mix 13.0 g of finely divided reagent grade stannic oxide, 394.0 g of finely divided reagent grade zinc oxide and 496.0 g of flame-hydrolyzed alumina for 15 minutes. The dry mix was stirred with sufficient deionized water (about 1 liter) to obtain a paste which was subsequently dried in an oven for 2½ hours at 392° F. After cooling, the dried material was found and sieved to obtain particles of less than 30 mesh in size. The sieved fraction was tested and found to contain 5.15 wt % water. It was mixed with Secar 71 ® cement employing 10 g of the cement per 100 g of the sieved fraction calculated on a water-free basis. In this instance, 891.7 g of the ground material equivalent to 845.8 g of anhydrous material was mixed with 84.6 g of the cement and with 2 wt % of stearic acid as lubricant. This mixture was formed into 1/8 × 1/8 inch tablets by means of a Stokes BB2 tablet machine. The tablets were collected, steamed for 3 hours at 285° F. and calcined for 5 hours at 1550° F. The calculated composition of the calcined support was 89.6 wt % zinc aluminate, 9.1% calcium aluminate and 1.3 wt % stannic oxide. The average crush strength of the calcined tablets was 20 lbs. Based on mercury porosimetry measurement the pore volume was found to be 0.30 mL/g, the average pore radius was 167 Angstroms and the pore area was 31 m$^2$/g.

EXAMPLE III

Catalyst Preparation and Dechlorination

Individual portions of the calcined, pelleted support of Example II were impregnated with aqueous chloroplatinic acid solution sufficient to obtain finished catalyst samples containing 0.3 wt % platinum and 0.6 wt % platinum based on the dry compositions. The chloride level impregnated in the catalyst corresponding to the 0.3 wt % loading of platinum was 0.57 wt % and to the 0.6 wt % platinum loading was determined to be 0.93 wt %. A portion of the chloride (about 0.1 wt %) resulted from that already present in the alumina. The samples were dried for 3 hours at 285° F.

The samples to be dechlorinated according to the invention were first calcined for 2 hours at 1200° F. Twenty-five gram portions of each calcined, cooled catalyst were washed with hot water for 6 hours in a soxhlet extractor, then removed and dried.

The control samples were first washed with hot water for 6 hours in the soxhlet extractor, then removed, dried and calcined for 2 hours at 1200° F.

The chloride levels resulting from each dechlorination method along with the corresponding platinum levels were determined. The results are presented in Table I.

TABLE I

| | CATALYST DECHLORINATION | | | | | |
|---|---|---|---|---|---|---|
| | CONTROL | | INVENTION | | INVENTION | |
| OPERATION | Pt. | Cl. | Pt. | Cl. | Pt. | Cl. |
| Impregnating | 0.6 | 0.9 | 0.3 | 0.6 | 0.6 | 0.9 |
| Calcine[2] | — | — | — | 0.6 | — | 0.7 |
| Washing | — | 0.06 | — | — | — | — |
| Calcine[2] | — | 0.06 | — | — | — | — |
| Washing[1] | — | — | — | 0.03 | — | 0.04 |
| Final | 0.4 | 0.06 | 0.3 | 0.03 | 0.6 | 0.04 |

[1]Washing consists of 6 hours in a SOXHLET extractor with water as a solvent.
[2]Calcining consists of 2 hours at 1200° F.

The results illustrated in Table I clearly show that hot water washing effectively reduces the chloride content of both invention catalysts and control catalysts. However, the platinum level (0.6 wt % Pt) remains the same for the invention catalyst whereas the control catalyst lost 0.2 wt % Pt. The invention catalyst initially containing 0.3 wt % Pt retained its Pt level during the dechlorination process. Calcining the impregnated catalyst prior to dechlorination is therefore shown to be necessary to anchor platinum to the support.

The amount of water needed to decrease the chloride level of calcined catalyst containing 0.3 wt % Pt and 0.57% chloride to an acceptable level was determined with the soxhlet extractor containing 47 g of catalyst. The hot water needed was based on volumes of water per volume of catalyst. During the process, two 5 g samples were removed for chloride analysis. Although the sample removal altered the liquid to solids ratio somewhat it is believed that a good indication of the liquid volume needed for effective dechlorination was realized. The results are plotted in FIG. 2. They show that the initial 0.57 wt % chloride level was reduced to about 0.17 wt % with the first 10 volumes of water, to about 0.09 wt % with about 25 volumes of water and to about 0.05 wt % with about 43 volumes of water. The chloride content decreases rapidly with the first few volumes of water and then it becomes increasingly difficult to reduce chloride to attain the desired level of about 0.05 wt % or less.

EXAMPLE IV

Propane Dehydrogenation

A portion of the calcined, hot water washed catalyst of Example III containing 0.3 wt % Pt and an identical calcined but unwashed control catalyst also containing 0.3 wt % Pt were steamed for 20 hours at 1200° F. employing 16.8 liquid ml steam per minute, which is equivalent to 348 gas mL/minute at STP. A 5 g portion of each steamed catalyst was employed in propane dehydrogenation at 1112° F. in the substantial absence of oxygen using a laboratory catalytic reactor operating at 4 LHSV and 50 psig. A propane feed of 20 liquid mL/minute equivalent to 87 gas mL/minute at STP and steam of 16.8 liquid mL/minute were passed through the reactor. Each catalyst was broken in for 2 hours at test conditions with the feed and steam and then regenerated for 2 hours employing 100 mL air/minute and steam at 16.8 liquid mL/minute at test conditions. Each test cycle consisted of 20 hours on stream followed by 4 hours of regeneration. The performance of the catalysts was based on the second cycle test results and is shown in FIGS. 3, 4, 5 and 6. These results show the washed invention catalyst to be more active than the unwashed control catalyst.

Figure 3:
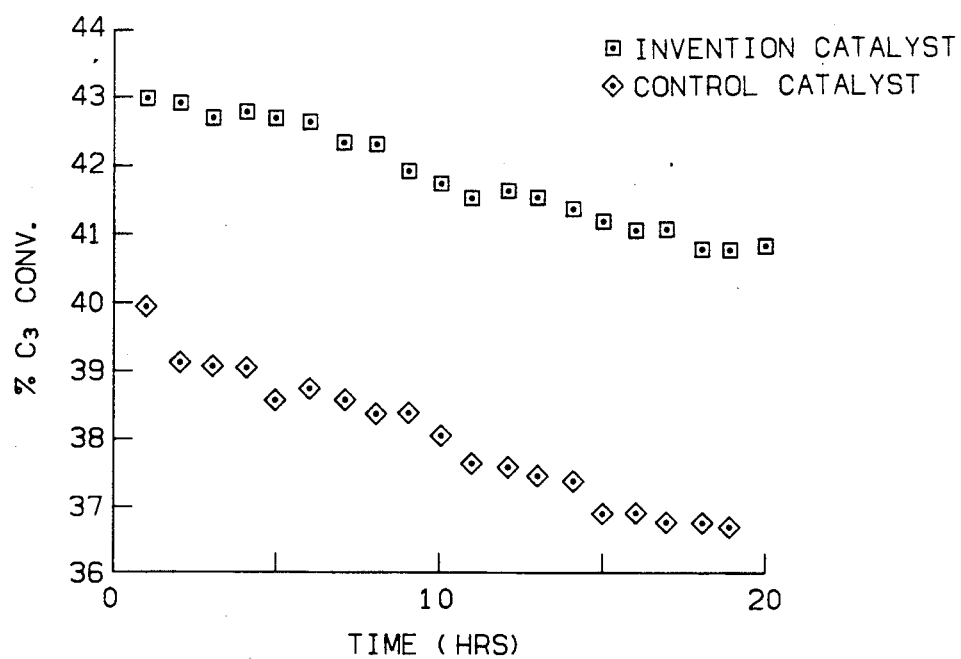
FIG. 3 is a graph illustrating propane conversion in a dehydrogenation process.
Figure 4:
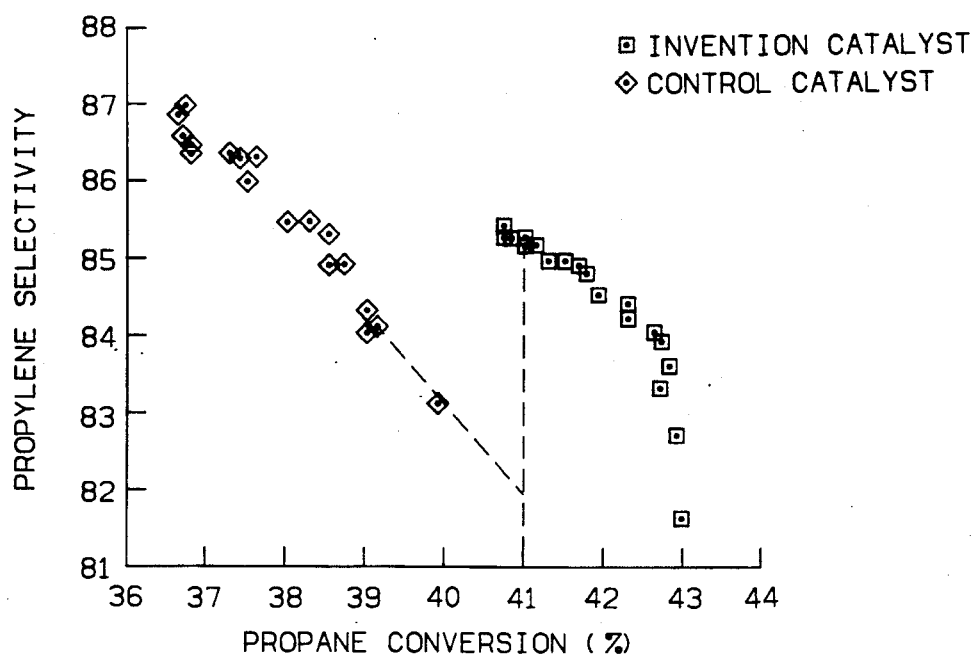
FIG. 4 is a graph illustrating propylene selectivity in a dehydrogenation process.

The ability of the catalyst to convert propane to propylene without producing large quantities of undesirable side products is the desired feature. The data presented in FIG. 3 show that the washed invention catalyst converts more propane to products than the unwashed control sample over the entire 20 hour test cycle. However, since the invention catalyst is always more active than the control catalyst, direct comparisons must come from interpolation of the selectivity data presented in FIGS. 4, 5, and 6. The data in FIG. 4 indicate for a given propane conversion, for example 41%, the selectivity of the unwashed control catalyst to propylene would be approximately 82% based on the extension of the curve, while the washed invention catalyst is about 85.5%.

Figure 5:
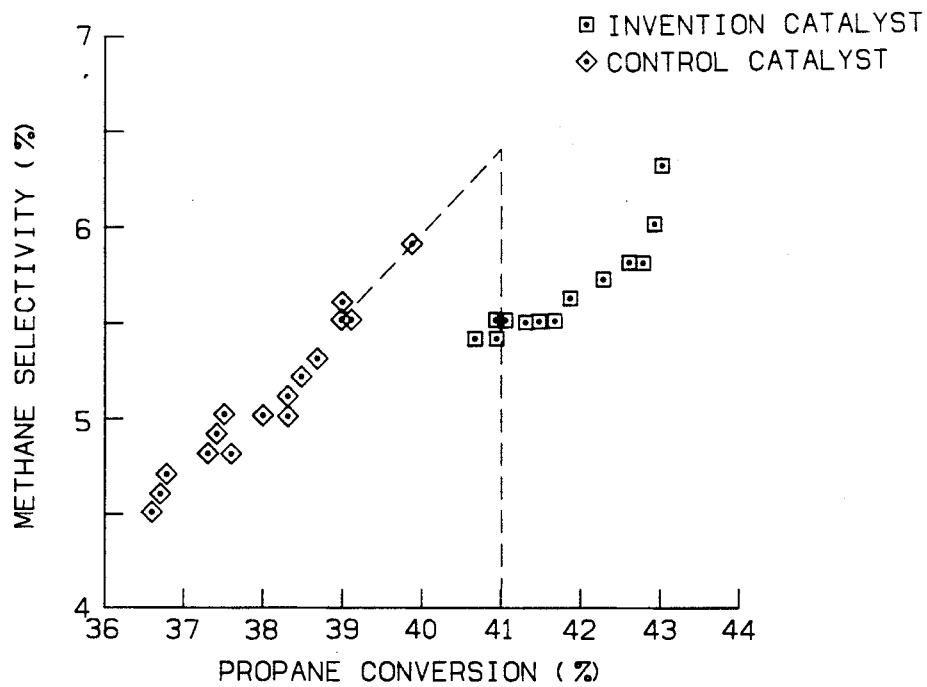
FIG. 5 is a graph illustrating methane selectivity in a dehydrogenation process.
Figure 6:
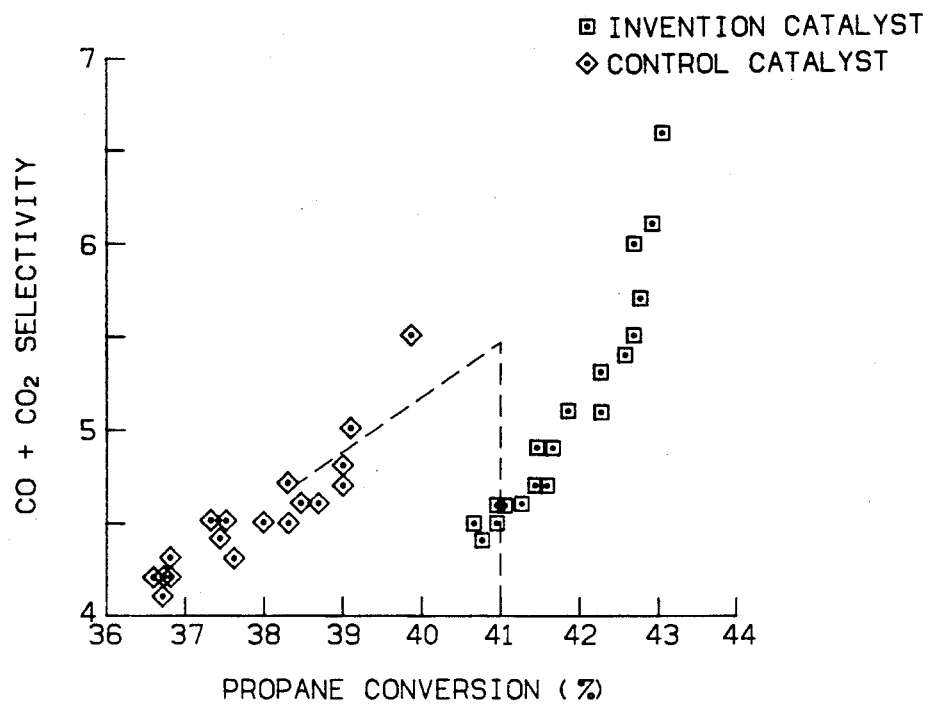
FIG. 6 is a graph illustrating carbon oxides selectivity in a dehydrogenation process.

FIGS. 5 and 6 show the catalysts production of undesirable methane and carbon oxides, which have very low values in the propane conversion process since it is desirable to minimize their production. The data in FIG. 5 show that at constant conversion, for example 41%, the selectivity to methane of the unwashed control catalyst would be approximately 6.4% based on the extension of the curve, while that of the washed invention catalyst is about 5.4%. The data in FIG. 6 show that at constant conversion the washed invention catalyst will produce less carbon monoxide and carbon dioxide than the unwashed control catalyst. Thus, based on extension of the curve for the control catalyst to the 41% level as before, the unwashed control catalyst selectivity to carbon oxides would be approximately 5.5% compared to that of the washed invention catalyst is about 4.5%.

The test results show that the invention catalyst exhibits better activity and selectivity in propane dehydrogenation than the control catalyst. Since both catalyst were steamed for 20 hours prior to testing the difference in results in believed to be a result of the hot water washing of the invention catalyst.

The above examples have been provided merely to illustrate the practice of our invention and should not be read so as to limit the scope of the appended claims in any way. Reasonable variations and modifications not departing from the essence and spirit of the invention, are contemplated to be within the scope of patent protection desired and sought.

That which is claimed is:

1. A process for preparing a dehydrogenation catalyst, said process comprising the following steps performed in the sequence set forth:
    (a) impregnating a porous zinc aluminate catalyst support containing calcium aluminate with a solution containing a compound of platinum with chlorine to form a supported catalyst;
    (b) drying the supported catalyst of step (a);
    (c) calcining the dried catalyst of step (b); and
    (d) washing the calcinated catalyst of step (c) with a wash media under conditions sufficient to remove substantially all chloride ions from said support while retaining substantially all platinum contained on said support, thereby producing said dehydrogenation catalyst wherein the chlorine content is less than about 0.05 weight percent.

2. A process in accordance with claim 1, wherein said impregnating step (a) is conducted by treating said catalyst support with an aqueous chloroplatinic acid solution at a temperature of from about 50° F. to about 122° F. for a time of about 1 second to about 1000 seconds, employing a platinum concentration in said aqueous chloroplatinic acid solution to achieve a platinum content of about 0.1 wt % to about 5.0 wt % of said support in said dehydrogenation catalyst.

3. A process in accordance with claim 2, wherein drying step (b) is conducted at a temperature of about 228° F. to about 342° F. and said calcining step (c) is conducted at a temperature of about 960° F. to about 1440° F.

4. A process in accordance with claim 3, wherein said dehydrogenation catalyst of step (d) contains about 0.3 wt % to about 0.6 wt % platinum.

5. A process in accordance with claim 4, wherein said porous support contains about 89.6 wt % zinc aluminate, about 9.1 wt % calcium aluminate and about 1.3 wt % stannic oxide.

6. A process in accordance with claim 4, wherein said porous support is an extruded support.

7. A process in accordance with claim 4, wherein said porous support is a tableted support.

8. A process in accordance with claim 1 wherein the volume of wash medium employed varies within the range of about 10 volumes of liquid wash medium per volume of catalyst to about 43 volumes of wash medium per volume of catalyst.

9. A process in accordance with claim 1, additionally comprising the following steps which are performed prior to step (a):
    blending a mixture of finely divided stannic oxide and finely divided zinc oxide, stearic acid, and optionally calcium aluminate cement to form a dry mixture;
    blending a mixture of alumina, deionized water and acetic acid to form a slurry of alumina;
    slowly adding said slurry of alumina to said dry mixture to form an extrudable composite composition;
    extruding said extrudable composite composition to form short strands of extrudate; and
    drying and calcining said extrudate to form said porous catalyst support.

10. A process in accordance with claim 9 wherein the chlorine content of the supported catalyst of step (a) is between about 0.6 weight percent and about 0.9 weight percent.

11. A process in accordance with claim 10 wherein washing step (d) is conducted for a period of time of about 6 hours.

12. A process in accordance with claim 1 wherein said solution comprises an alcoholic solution of chloroplatinic acid.

* * * * *